(12) United States Patent
Wrigglesworth et al.

(10) Patent No.: US 10,993,668 B2
(45) Date of Patent: May 4, 2021

(54) SAMPLING DEVICE

(71) Applicant: Mars, Incorporated, McLean, VA (US)

(72) Inventors: David Wrigglesworth, Waltham-on-the-Wolds (GB); Timothy McKnight, Oak Ridge, TN (US); Milton Nance Ericson, Oak Ridge, TN (US)

(73) Assignee: Mars, Incorporated, McLean, VA (US)

( * ) Notice: Subject to any disclaimer, the term of this patent is extended or adjusted under 35 U.S.C. 154(b) by 353 days.

(21) Appl. No.: 14/777,143

(22) PCT Filed: Mar. 14, 2014

(86) PCT No.: PCT/EP2014/055196
§ 371 (c)(1),
(2) Date: Sep. 15, 2015

(87) PCT Pub. No.: WO2014/140334
PCT Pub. Date: Sep. 18, 2014

(65) Prior Publication Data
US 2016/0038086 A1    Feb. 11, 2016

(30) Foreign Application Priority Data

Mar. 15, 2013   (GB) ...................................... 1304738

(51) Int. Cl.
*A61B 10/02* (2006.01)
*A61B 17/00* (2006.01)
(Continued)

(52) U.S. Cl.
CPC ............ *A61B 5/6861* (2013.01); *A61B 5/073* (2013.01); *A61B 5/14507* (2013.01);
(Continued)

(58) Field of Classification Search
CPC .............. A61B 5/6861; A61B 5/14539; A61B 5/14507; A61B 10/0038; A61B 10/0045;
(Continued)

(56) References Cited

U.S. PATENT DOCUMENTS

| 3,118,439 A | 1/1964 | Perrenoud |
| 3,485,235 A | 12/1969 | Felson |

(Continued)

FOREIGN PATENT DOCUMENTS

| CN | 1454571 A | 11/2003 |
| DE | 19801573 | 7/1999 |

(Continued)

OTHER PUBLICATIONS

Eddington et al., Flow control with hydrogels, Advanced Drug Delivery Reviews, vol. 56, 2004, pp. 199-210.*

(Continued)

*Primary Examiner* — Jacqueline Cheng
*Assistant Examiner* — Tho Q Tran
(74) *Attorney, Agent, or Firm* — Mars, Incorporated (57) ABSTRACT

The present invention relates to a device for sampling internal substance(s) in the gastrointestinal tract of an animal composed of at least one wall which is partially expandable. The invention also relates to a method of orally administering the device to an animal and recovering the device from the stool to carry out analysis on the collected sample for diagnosing the health of the gastrointestinal tract and determining nutrient absorption and digestibility.

13 Claims, 5 Drawing Sheets

(51) Int. Cl.
  *A61B 10/00* (2006.01)
  *A61B 5/00* (2006.01)
  *A61B 5/145* (2006.01)
  *A61B 5/07* (2006.01)

(52) U.S. Cl.
  CPC ...... *A61B 5/14539* (2013.01); *A61B 10/0038* (2013.01); *A61B 10/0045* (2013.01); *A61B 10/02* (2013.01); *A61B 10/0283* (2013.01); A61B 2010/0061 (2013.01); A61B 2010/0083 (2013.01); A61B 2010/0208 (2013.01); A61B 2017/00035 (2013.01); A61B 2017/00084 (2013.01); A61B 2017/00411 (2013.01); A61B 2017/00734 (2013.01); A61B 2017/00818 (2013.01); A61B 2503/40 (2013.01); A61B 2560/0214 (2013.01); A61B 2562/162 (2013.01)

(58) Field of Classification Search
  CPC ..... A61B 10/02; A61B 10/0283; A61B 5/073; A61B 2562/162; A61B 2560/0214; A61B 2503/40; A61B 2010/0208; A61B 2010/0083; A61B 2010/0061; A61B 2017/00035; A61B 2017/00084; A61B 2017/00734; A61B 2017/00818; A61B 2017/00411
  See application file for complete search history.

(56) References Cited

U.S. PATENT DOCUMENTS

| | | | |
|---|---|---|---|
| 3,837,199 | A | 9/1974 | Larsonneur |
| 4,186,730 | A | 2/1980 | Bucalo |
| 4,239,040 | A | 12/1980 | Takeshi et al. |
| 4,481,952 | A | 11/1984 | Pawelec |
| 5,395,366 | A * | 3/1995 | D'Andrea ............ A61B 5/0031 604/114 |
| 5,443,459 | A | 8/1995 | Wong et al. |
| 5,971,942 | A | 10/1999 | Gu et al. |
| 6,564,087 | B1 | 5/2003 | Pitris et al. |
| 7,160,258 | B2 | 1/2007 | Imran et al. |
| 7,611,480 | B2 | 11/2009 | Levy |
| 8,394,034 | B2 | 3/2013 | Iddan et al. |
| 8,444,572 | B2 | 5/2013 | Tanaka |
| 8,562,589 | B2 | 10/2013 | Imran |
| 8,636,648 | B2 | 1/2014 | Gazdzinski |
| 8,870,767 | B2 | 10/2014 | Bulitta et al. |
| 10,172,598 | B2 | 1/2019 | Amoako-Tuffour et al. |
| 2002/0055734 | A1* | 5/2002 | Houzego ............... A61M 25/01 604/891.1 |
| 2004/0267240 | A1 | 12/2004 | Gross et al. |
| 2006/0069317 | A1* | 3/2006 | Horn ...................... A61B 1/041 600/300 |
| 2006/0246510 | A1* | 11/2006 | Densham ............. G01N 21/554 435/7.1 |
| 2007/0161928 | A1 | 7/2007 | Sprenkels et al. |
| 2007/0173738 | A1* | 7/2007 | Stoltz ................. A61B 10/0045 600/582 |
| 2008/0146871 | A1* | 6/2008 | Arneson .............. A61B 5/0002 600/101 |
| 2011/0105864 | A1* | 5/2011 | Robertson ............ A61B 5/0031 600/302 |
| 2012/0203084 | A1 | 8/2012 | Li et al. |
| 2014/0287966 | A1* | 9/2014 | Gray .................... F16K 99/0032 506/39 |
| 2015/0011874 | A1 | 1/2015 | Amoako-Tuffour et al. |
| 2017/0252016 | A1 | 9/2017 | Wrigglesworth et al. |
| 2017/0252017 | A1 | 9/2017 | Wrigglesworth et al. |
| 2017/0252018 | A1 | 9/2017 | Wrigglesworth et al. |

FOREIGN PATENT DOCUMENTS

| | | |
|---|---|---|
| JP | S5149588 A | 4/1976 |
| JP | 52131678 | 11/1977 |
| JP | S5376584 U | 6/1978 |
| JP | S53076584 | 7/1978 |
| JP | H04176443 A | 6/1992 |
| WO | 2005024436 B1 | 3/2005 |
| WO | 2005046485 | 5/2005 |

OTHER PUBLICATIONS

Hammond et al., "A system-on-chip digital pH meter for use in a wireless diagnostic capsule," IEEE Transaction on Biomedical Engineering, 2005, 52(4):687-694.

Johannessen et al., "Implementation of multichannel sensors for remote biomedical measurements in a microsystems format," IEEE Transaction on Biomedical Engineering, vol. 51, pp. 525-535, Mar. 2004.

Twomey et al., "Swalloable capsult technology: Current perspectives and future directions," Endoscopy 2009, 41(4):357-362.

* cited by examiner

SAMPLING DEVICE

STATEMENT REGARDING FEDERALLY SPONSORED RESEARCH

This invention was made with government support under Contract No. DE-AC05-000R22725 awarded by the U.S. Department of Energy. The government has certain rights in the invention.

CROSS REFERENCE TO RELATED APPLICATIONS

This application is a national stage application, filed under 35 U.S.C. § 371, of International Application No. PCT/EP2014/055196, filed Mar. 14, 2014, which claims priority to Great Britain Patent App. Serial No. 1304738.6 filed on Mar. 15, 2013, the entire contents of each being incorporated by reference herein for any and all purposes.

The present invention relates to a device for sampling internal substance(s) in the gastrointestinal tract of an animal composed of at least one wall which is partially expandable. The invention also relates to a method of orally administering the device to an animal and recovering the device from the stool to carry out analysis on the collected sample for diagnosing the health of the gastrointestinal tract and determining nutrient absorption and digestibility.

The ability to directly sample substance within the gastrointestinal tract in an animal is a key enabling technology for diagnosing the health of the gastrointestinal tract, determining in vivo ilea protein digestibility and for investigating the relationship between specific dietary components and the chemical and physico-chemical properties in the gastrointestinal tract of animals. This includes nutrient absorption, drug metabolism, microorganism distribution, and so on.

Analysing a sample of substance, such as a gas, a solid particle or a liquid from the gastrointestinal tract of an animal, provides information on the pH, enzyme activity, and nutrient composition of the sampled material as well as information for diagnosing diseases of the gastrointestinal tract and microorganism distribution.

Early detection, identification of and location of abnormal conditions can be critical for definitive diagnosing and/or treating various pathologies.

Also, ilea protein digestibility is an important factor in diet design since protein fermentation by the intestinal flora within the colon has been associated with the formation of toxic compounds, including ammonia, di-hydrogen sulphide, in-doles and phenols, which have been shown to increase the risk of colon cancer in humans. In the design of "production animal diets", it is also important to minimise the cost of the diet and the environmental impact of waste products from the animal.

Whilst total apparent digestibility (as measured in faeces) is a key measure, this methodology has a number of shortcomings, including relevance and accuracy, particularly when assessing protein digestibility. Ilea digestibility is therefore a more appropriate measure of nutrient delivery. The outflow of the terminal ileum into the caecum can be considered as the substrate upon which the hind gut microflora act. Consequently the ability to measure a broad range of chemical (e.g. protein, carbohydrates, fibre, non-starch polysaccharides, anti-nutritional factors, fats) and physiochemical (e.g. viscosity) properties from within the ileal digesta also represents a significant step-change in our understanding of the effects of specific dietary components on digestive processes and faeces quality, in addition to providing further diagnosing and research treatments specific to the gastrointestinal disease of the particular subject.

Conventional methodologies for investigating ilea digestibility in vivo through collection of ilea digesta include those that require surgical modification to enable repeated sampling of the ilea digesta or the sacrifice of study animals.

Gastrointestinal substance samples are usually taken using intubation mechanical devices, such as endoscopes, which are expensive, time consuming and which may cause pain and anxiety to the subject under examination. Collection of ilea digesta samples from animals by intubation is currently the preferred option, as it represents the most reliable and accurate methodology currently available.

In particular, intubation endoscopy is unpleasant, both physically and psychologically, and usually requires local anaesthetic and sometimes sedation.

Devices, systems, and methods for in vivo sensing of passages or cavities within a body and in particular the gastrointestinal tract, and for sending and gathering information (for example: images, pH information, temperature information, electrical impedance information, pressure information, etc.) are known in the art.

Swallowable capsules which either collect biometric data (e.g. temperature, pH, conductivity, dissolved oxygen, velocity) during transit through the gastrointestinal tract or deliver targeted doses of medicine to patients or even produce images of the entire gastro intestinal tract are known in the art. For example, the PillCam™ SB manufactured by Given Imaging Ltd. (Yoqneam, Israel) is 11 mm×26 mm and weighs less than 4 grams. The PillCam™ contains an imagining device and light source on one side and transmits images at a rate of 2 images per second and is used by physicians to detect and diagnose disorders of the small intestine.

Further the iPill made by Philips (Philips Research, AE Eindhoven, The Netherlands) is a camera pill, similar in size to the PillCam™ and is suitable to deliver targeted doses of medicine to patients. In addition to image collection and drug delivery, similar capsule technologies exist which can collect biometric data (e.g. temperature, pH, conductivity, dissolved oxygen, velocity) during transit through the gastrointestinal tract (Johannessen et al., 2004; Hammond et al., 2005; Twomey & Marchesi, 2009).

Devices for sampling liquids from the gastrointestinal tract are known in the art. WO02/102243 and U.S. Pat. No. 5,971,942 both describe a device for sampling the gastrointestinal tract. The interior of the capsule is under vacuum and allows sample to be drawn in through an inlet. The sample enters the inside of the capsule until the pressure between the inside and outside of the capsule is equalised and the inlet and/or blocking member prevents the outward flow of the sample.

US2007/0161928 is another sampling device wherein the body of the device is a channel with one or more compartments and is able to capture small amounts of the gastrointestinal tract at different points.

These known devices either have one large chamber or small multiple compartments which draw sample(s) from the gastrointestinal tract.

The device of the invention is able to collect a larger amount of sample than the devices in the prior art as a result of its expandable wall that elongates the device to an open expanded state.

A closure tab which holds the device in the compressed state can be passively actuated or actively actuated, by means of a digestible coating, a pH timer/sensor or an external force which actuates a switch to the open expanded state at a given point. This enables good control of the timing for opening of the device. The opening can be pre-programmed or externally controlled.

There is an ongoing need to improve sampling devices as described above, such that a larger volume of sample may be acquired, allowing a greater range of analytical tests to be carried out on the sample. Furthermore, the ability to alter the point within the ileum at which the sample is captured allows investigation of the changes in nutrient absorption, microbial population, digesta viscosity throughout the length of the ileum.

The present inventors have devised a device which can be used to acquire a large volume of internal substance from the gastrointestinal tract of an animal, which is non-invasive, requires no surgical procedure, is appropriate to use without the need to sedate the animal being tested or causing them any pain. The device of the present invention is simple, inexpensive, reliable and easy to use, without the need of constant monitoring. The device of the present invention can be recovered from the stool and the sample easily extracted and analysed using a variety of biological, chemical and physical assays.

In a first aspect of the invention there is provided a device for sampling internal substance in the gastrointestinal tract of an animal, said device comprising of at least one wall which is at least partially expandable wherein, said device is held in a closed compressed state by a closure tab, a receptacle and an actuator means for assisting in drawing the sample into the device, when the closure tab is in place the device is in a closed compressed state, when the closure tab is not in place the device is in an open expanded state. In particular, when the closure tab is not in place the wall of the device is movable to an open expanded state by the actuating means.

In particular, the actuator means is arranged to convert the device from a first configuration (for example: a closed compressed state) to a second configuration (for example: an open expanded state) and assists in drawing the sample into the device.

The device of the invention is therefore suitable for sampling of internal substance in the gastrointestinal tract of an animal. Depending on the animal, size, breed and/or species, the device will vary in size as described herein.

The ability to directly sample the substance within the gastrointestinal tract in an animal is a key enabling technology for diagnosing the health of the gastrointestinal tract, determining in vivo ilea protein digestibility and for investigating the relationship between specific dietary components and the chemical and physico-chemical properties in the gastrointestinal tract of animals, for example nutrient absorption, drug metabolism, microorganism distribution, and so on.

The terms "substance" and "internal substance" are used interchangeably and refers to any liquid, particle or gas, which can be found in the gastrointestinal tract of an animal. Liquid can for example be found in the stomach, small and large intestine. Such liquids may contain species in solution (or suspensions) such as dietary components, drugs, food components; digestion products, microbial metabolites, gases, such as oxygen, hydrogen, carbon dioxide, methane, hydrogen sulphide, etc. can also be found.

In particular, the expandable wall is movable from a closed compressed state to an open expanded state.

The device is composed of at least a partially expandable wall.

In one embodiment, the partially expandable wall is corrugated. In particular, the expandable wall is corrugated or substantially corrugated when the device is in a closed compressed state, when the device in an open expanded state the wall elongates to convert the device into a second open expanded state, wherein the wall is partially flattened.

In another embodiment, the expandable wall is flat or substantially flat when the device is in a closed compressed state. When the device is in an open expanded state the wall slides and the device is converted to a second open expanded configuration state.

In some embodiments, the device can comprise two halves connected at least to one another by one or more elements. In particular the two halves may be connected to one another by an internal tether filament, or similar.

In particular, the device is able to capture a sample of digesta during the transit along the gastrointestinal tract of the animal. The device must be able to withstand peristalsis of the gastrointestinal tract.

Typically, the device can be made of any, non-digestible, non-biodegradable, non-immunogenic, non-bioreactive or impermeable material. In particular, the material used to make the device can be any biologically inert polymeric materials acrylonitrile butadiene styrene (ABS) or made from other biologically inert material, such as polytetrafluroethylene, polethylene, acrylics and the like, ceramics or metals, for example stainless steel, preferably smooth and/or radio opaque.

In particular, the material used determines the external texture and/or hardness of the device. The material can be hard, soft, smooth and/or malleable and the preference of the material used is dependent on its use.

In some embodiments, the device is in a shape of a capsule or a pill. The capsule can be cylindrical with rounded, conical or flattened ends. The pill can be partially spherical in shape.

In particular, the device is preferably suitable for swallowing. Capsules known in the art have dimensions of 11 mm×26 mm (width×length), such as the PillCam™ or the iPill. The particular advantage of the present invention is the expandable wall which enables the device to be in a first closed compressed state for swallowing and movable to a second open expanded state inside the body, e.g. gastrointestinal tract.

In some embodiments, in the closed compressed state the dimensions of the device can be in the range of 5 mm×15 mm (width×length) to 15 mm×30 mm (width×length), preferably a maximum length of 26 mm. The length of the device in the closed compressed state is important in order for the device to be suitable for swallowing. In particular, the width of the device can range from 5 mm to 15 mm and/or the length can range from 15 mm to 30 mm and/or combinations thereof.

The length of the device expands as a result of the expandable wall. The expandable wall elongates the device from its first closed compressed state to its second open expanded state. In some embodiments, the dimensions of the device in the open expanded state can be in the range of 5 mm×30 mm (width×length) to 15 mm×50 mm (width×length). In particular, the expandable wall can elongate the device by a maximum of 20 mm from its original length when in its closed compressed state. In particular, the width of the device can range from 5 mm to 15 mm and the length of the device in its expandable state can range from 30 mm to 50 mm and/or combinations thereof.

Typically, the device may comprise a printed circuit board which contains a microcontroller and a diode based communication port, such printed circuit is readily known in the art.

In some embodiments, the printed circuit may further comprise a pH circuit. The circuit can log the pH level during the transit of the device along the gastrointestinal tract. Further, the pH circuit can also log the actuation moment when the device elongates from its first closed compressed state to its second open expanded state.

In some embodiments, the device may further include a pH sensor, a temperature sensor, a pressure sensor, an ultra sound sensor or the like.

In some embodiments, the device comprises at least one battery and associated electronic circuits. The battery may be rechargeable. In other embodiments, the device can be reusable. The part of the device which contains the pH-sensor, circuitry and batteries may be reusable.

In other embodiments, the device may further comprise a pH sensing apparatus connected to the battery and the associated electronic circuits.

In further embodiments, the device may comprise a switch, such as a tether filament connected to the battery and the associated electronic circuit. In particular embodiments, the device may comprise a combination of a pH sensor, switch, battery and electronic circuit.

The device of the invention comprises a closure tab, which can be passively or actively activated.

The closure tab of the device of the invention can be any substance or composition or object which is capable of holding the device in compression, preferably for a predetermined time in various predetermined conditions.

In particular, the device can be held in a closed compressed state by a closure tab. In particular the closure tab may be a coating, an internal tether filament, a pH sensor or a switch.

In particular, the closure tab can be activated remotely from outside the body, or can be pre-programmed based on time, or can be activated based on other physiological characteristics, such as pH, pressure, temperature, enzymatic activity, etc.

In other embodiments, the closure tab can be activated in response to specific conditions such as, for example, time, location, environmental conditions, etc.

In further embodiments, the device may include a controller which controls the closure tab. In particular, the controller may either generate a signal at a predetermined time or may receive a signal externally or generate a signal in response to sensed parameters, such as pH, temperature, pressure, enzyme activity, or the like which activates the closure tab. Other suitable methods of controlling the closure tab may be used.

When the closure tab is activated either by acid, alkaline or external remote activation, the closure tab disintegrates and/or triggers the device to be controllably released from a closed compressed state into an open expanded state.

In some embodiments, the closure tab can be an external coating.

In particular embodiments, wherein the closure tab is a coating, the coating may surround the entire device or the coating may partially cover the device. The coating may at least cover the connection between the two halves.

Typically a coating is any material which dissolves upon contact with internal substance in the gastrointestinal tract. In particular, such a coating may be dependent on the pH conditions of the internal substance in contact. The coating can be made of two or more layers of the same material or of different materials. The material dissolves gradually upon contact with different internal substances during the transit along the gastrointestinal tract.

The coating may comprise and/or consist of a pH-sensitive material that degrades in an alkaline environment. The rate of degradation may be controlled by either differences in the chemical structure of the material or by differences in the thickness application and/or form of similar materials, or both.

In some embodiments, a first coating material/layer is dissolved in response to a first pH, first temperature, first pressure or first enzymatic activity, and a second coating material/layer is dissolved in response to a second, different pH, different temperature, different pressure or different enzymatic activity.

The external coating can be pH dependent and dissolve in the stomach when in contact with gastric acid and in acidic conditions under pH 4 or in the large intestine when in alkaline conditions such as a pH5-6 or above 7.

In particular embodiments, the external coating can be made of material such as cellulose, acetate phthalate, glycerol stearates, paraffin, epoxy compounds or poly (methyl) acrylates, such as Eudragit® L, S or E. Preferably, the external coating is Eudragit® L, S or E.

In other embodiments, the closure tab can be a pH sensor.

Typically, a pH sensor is dependent on the pH condition in which it is embedded, which can be pre-programmed to react/respond to a certain pH condition depending on the location along the gastrointestinal tract. The pH sensor can be preprogrammed to activate at pH levels of 1, 2, 3, 4, 5, 6, 7, 8, 9, 10, 11, 12, 13 or 14 and/or any ranges and/or combinations thereof. For example, a pH below 4 can be preprogrammed so that the device expands to its second open configuration in the stomach, or preprogrammed at pH above 5 so that the device expands to its second open configuration in the small or large intestines.

In yet other embodiments, the closure tab can be a switch that can be externally electromagnetically operated or be activated by an internal clock that is pre-programmed.

The closure tab may also be an internal filament having a heat-degradable element that is degraded by the localized heat produced by discharge of an on-board battery. In this case, the closure tab can be degraded at a pre-programmed time by the control of the battery discharge by the electronic controls within the device.

The closure tab may be externally actuated by means of a magnetic reed switch or similar device. Actuation is achieved by the animal passing through an electromagnetic field, for example an array of copper coils or by the application of an electromagnetic field. The subsequent closure of the magnetic switch causes the on-board battery to discharge across a thermally-sensitive element used to hold the device in a compressed configuration, resulting in the degradation of this element and the expansion of the device to the second configuration i.e. to an open expanded state. A similar actuation of the device may be achieved by pre-programming the time interval preceding the battery discharge, such that the sample capture takes place at a predetermined time after the pH sensor detects a rise in pH associated with the exit of the device from the stomach of the animal. In this case, an external electromagnetic triggering is not required.

The device of the present invention comprises an actuator means. An actuator means can be a resilient member. In particular, it may be any object that is capable of storing kinetic energy. In particular embodiments, the actuator means is a spring.

In some embodiments, the device may further include a controller which controls the actuator means.

Typically a resilient member encompasses any object which is capable of returning to its original form or position after being bent, compressed or corrugated. A resilient member is therefore capable of storing kinetic energy. A resilient member includes a spring.

Typically a spring is an elastic object, such as a coil of wire, which regains its original shape after being compressed or extended.

In other embodiments, the actuator means is activated at specific conditions, such as, for example, time, location, environmental conditions, etc dependent on the chosen closure tab activation.

The spring acts as an actuating means. The spring is held in compression when the closure tab is in place. The device is held in a a closed compressed state by the closure tab. When the closure tab is not in place and is therefore activated (either passively or actively), the spring acts as the driving force in drawing the sample into the device as well as expanding the device from its first closed compressed configuration to the second open expanded configuration. The driving force of the spring creates a short time framed vacuum as the device expands and the spring is released and/or a capillary action in which the sample is drawn into the receptacle, preferably into the chamber through an external aperture.

The actuator means may be activated in response to a predetermined signal from the internal processor and/or controller in the device.

In particular embodiments, the actuator means may be activated in response to a signal from an external controller.

A signal may be generated by the internal processor or external controller which activates the actuator means to convert the device from a first closed compressed configuration to a second open expanded configuration.

The motion of elongating the device is caused by the actuator means. The actuator means therefore draws sample into the receptacle and preferably into the sample collecting chamber.

In particular embodiments, the device comprises one or more inlets, which allow part of the sample to be drawn into the receptacle, preferably into the sample collecting chamber.

In some embodiments, the length or diameter of the aperture is from 2 to 5 mm.

The aperture can be arranged to be at the midpoint of the device. In particular embodiments, in the compressed configuration, no aperture is visible. When the device is expanded into its open expanded state the aperture is exposed to the external environment. The aperture can be at the end of the receptacle or end of the sample collecting chamber. The aperture may be at different locations along the device The device further comprises a receptacle. The receptacle comprises at least one sample collecting chamber. In some embodiments, the chamber or chambers of the device of the invention is/are external flexible balloon structure/s.

Further, the receptacle may comprise one or more aperture(s). In some embodiments, the aperture can be an external aperture or an internal aperture that is situated within the device.

The chamber can be enclosed within the device by compression of the spring wherein the chamber is composed of the spring and a balloon structured arrangement. In other embodiments the chambers can be an external sample collecting chamber which is secured to the outside of the device by a layer of coating.

In some embodiments, the device is in an open expanded state; at least one of the chambers can have a volume of up to 5 ml. Sampling volumes of greater than 5 ml are unlikely, given the restriction in passing through the ileo-caecal junction (small intestine to large intestine). At volumes greater than 5 ml, it is more likely that a blockage may occur at this point, which is undesirable.

In some embodiments, the device can have a receptacle that includes a first sample collecting chamber to collect a first sample at a first determined point in the gastrointestinal tract and a second sample collecting chamber which collects a second sample at a second determined point in the gastrointestinal tract.

In some embodiments, the receptacle may include a sample collecting chamber having a reagent or marker to interact with the collected sample. The sample containing chamber is one-use only, as it is destroyed when the sample is recovered.

In some embodiments, the device of the present invention includes means for closing one or more apertures.

In preferred embodiments, the means for closing is an expandable object, preferably a polyacrylamide bead.

The polyacrylamide bead is immobilized on a mesh screen behind the sampling aperture. In the compressed state of the device, the bead is in a dehydrated state and is protected from the environment of the stomach/intestinal lumen. When the closure tab is activated to release the actuator means and the expandable wall elongates the device to an open expanded state the bead is exposed to an aqueous environment and over a short period of time swells to its hydrated state, blocking the sample aperture and therefore securing the captured sample within the device.

A closing means may be a passive closing means, for example, an autonomous closing means, a non-controllable closing means, a closing means which is able to partially open/close one or more of the apertures or a closing means which is not controlled after entering the body of the animal. Alternatively, the closing means may be an active closing means, for example a controlled closing means, a non-autonomous closing means, a closing means which is able to partially open/close one or more of the apertures controlled or triggered by external user, device or system and/or a closing means which uses an active opening and closing mechanism (e.g. mechanical, electronic, or magnetic mechanism) or the like. Other closing means known in the art may also be used.

A second aspect of the invention provides a method of obtaining internal substance from the gastrointestinal tract of an animal, comprising the following steps; orally administering the device of the invention to the animal, and recovering the device from the stool of the animal. The device orally ingested by the animal is recovered from the stool and the sample is easily extracted. The sample is preserved and recovered from the device to perform various biological, chemical and physical tests, such as total nitrogen tests for protein, amino acid analysis using high performance liquid chromatography, measuring the size of the peptides, for example by gel permeation chromatography, etc.

In some embodiments, the capsule is administered to the animal in a fasting state, with food or at an interval after feeding.

In some embodiments, the method of the invention is carried out on an animal. An animal includes humans, pets such as a dog, cat or horse or farm animals such as a cow, sheep or a chicken.

Modifications to the device may be necessary according to the species on which it used. In particular, smaller devices would be required for smaller animals. Differences in gastrointestinal pH-profile also need to be accounted for, in particular in the case of ruminants.

Methods of detecting the device during its transit along the gastrointestinal tract of an animal are readily known in the art, such as the use of radiography or ultrasound.

Descriptive Use of the Invention

1) The device has been demonstrated to be safe for ingestion by non-fasted healthy adult large breed dogs:
   All components are of a suitable medical grade and assessed to be of low toxicological risk using an appropriate risk assessment methodology (e.g. quantitative risk assessment).
2) The device has demonstrated in in vitro and in in vivo to sample substance representative of the terminal ileum across the likely range of fiber and protein interventions planned within the digestive function competency.
   In vitro—the samples collected by the device in vitro are equivalent, within the error of the analytical measurement for a specific analyte, to the milieu in which it is located at the time of sampling, where the solutions and mixtures tested have physiological relevance.
   In vivo—the samples collected by the device in vivo are equivalent, within the between-dog error for a specific analyte, to samples collected from the terminal ileum of dogs (e.g. post-euthanasia).
3) The device is able to recover larger sample from the terminal ileum of healthy adult large breed dogs for the determination of ilea protein digestibility.

The invention will now be further described by way of reference to the following Examples and Figures, which are provided for the purpose of illustration only and are not to be construed as being limiting on the invention. Reference is made to a number of Figures in which.

EXAMPLE 1

Passive Actuating Mechanism

Spring-loaded capsules were held together with Eudragit L-100 (pH 6.0)+\-cellulosic wraps (to distribute loading force).

Capsules were subjected to a 24 hour period of gastric acid simulant (pH 1), followed by temporal evaluation of actuation after bicarbonate adjustment of solution to pH 7.0. Dissolution of the enteric coating appears to be highly variable.

The results obtained with different coatings and at different time intervals are detailed in table 1 below.

TABLE 1

| Coating | Time to Opening (Hrs) | | | |
|---|---|---|---|---|
| Cellulose wrap wetted | 0.5 | 1.75 | 24+ | 24+ |
| Cellulose wrap and pill wetted | 24+ | 24+ | 24+ | 24+ |
| No Wrap | 2.5 | 4 | 24+ | 24+ |
| No Wrap | 1.5 | 3.25 | 7.25 | 24+ |

EXAMPLE 2

Active Actuating Mechanism

Capped samplers were compressed and placed under solution and released 10 minutes later, the unit exteriors are washed and weighed to determine the amount of sample captured.

Further, the capped samplers with an internal spring and inlet restriction (without polyacrylamide bead) were compressed and placed under various viscosity solutions and allowed to expand for 1 minute. Contents were weighed to evaluate the amount of sample captured.

Table 2 below shows the amount of volume obtained, wherein the spring used is shown to be sufficiently robust to draw in a representative physiologic viscosity into the sampling chamber.

TABLE 2

| Spring | Theoretical max. volume | Water volume | Ilea digesta |
|---|---|---|---|
| 12405 | 1.69 | 1.32 +/− 0.5 | 1.02 +/− .14 |
| 3644 | 1.36 | 1.09 +/− .07 | 0.85 +/− .23 |

EXAMPLE 3

In Vivo Gastric Emptying Times

The following study investigates the measurement of normal gastric emptying time and gastrointestinal transit on Labradors using a barium meal and observations with an X-ray fluoroscopy.

The study panel consisted of 6 adult Labrador retriever. Each dog was orally administered a meal (standard wet PEDIGREE® with Tripe) containing the inert marker barium sulphate on three occasions across a 3-week trial period. The dogs were fed 50% of their daily maintenance energy ration mixed with barium sulphate at a concentration of 7% w/w. Fluoroscopy was then performed on 12 occasions per dog per assessment day in order to establish the gastric emptying and intestinal transit of the meal. These fluoroscopic examinations took place at +0 mins, +5 mins, +15 mins and +30 mins post administration of the barium meal, then at +1, +2, 3, 4, 5, 6, 7, and 8 hours. Dogs were individually housed between fluoroscopy procedures in order to ensure that coprophagia does not result in barium being transferred to another dog.

Fluoroscopy was carried out at the appropriate times using a GE Healthcare Fluorostar 7900 mobile x-ray C-arm system. Images were captured in 'Reduced Dose' mode to limit the x-ray dose delivered to the dog, with all dogs limited to a maximum dose of 2000 mGy*cm2 per week in order to ensure that no adverse skin effects were observed.

Images were captured in both lateral and ventrodorsal orientations to provide the appropriate level of information required to monitor the progress of the digesta/barium mix through the digestive tract. Exposure settings were controlled by the fluoroscope 'Autowindow' function.

Images were subjectively interpreted by a single observer in all cases, in order to assess the location of the digesta/barium mix within the digestive tract and the approximate 'fill density' of the digesta/barium mix in the stomach, small intestine and large intestine.

High fill density of the stomach was observed in most instances up to at least +30 mins post ingestion, with significant quantities remaining up to +1 hour and lesser quantities remaining at +2 hours and +3 hours. In most cases, the stomach contained only trace remnants of barium at +7 and +8 hours post ingestion.

In most instances, the first exit of barium from the stomach was observed at +30 mins post ingestions, appearing as discreet traces of radiodense material along the small intestine. The first exit of barium from the stomach was never observed earlier than +15 mins or later than +1 hour post ingestion. Since there was no significant emptying of the stomach observed over this timeframe, it is likely that the barium was carried in a liquid phase.

High fill density of the small intestine was observed to occur starting at +1 hour to +2 hours post ingestion in most instances, with significant quantities remaining up to at least +5 hours. Lesser quantities remained after +5 hours post ingestion, with only a very low fill density being observed in most cases after +7 and +8 hours post ingestion.

High fill density of the ascending colon was observed to occur starting at +3 hours post ingestion, with significant quantities throughout the ascending, transverse and descending colon from +4 hours post ingestion onward. Since defecation is under voluntary control, the colon either remained at a high filling density from +4 hours until the end of the observation period (+8 hours), or emptied at a point corresponding with defecation.

The objective of the study was to investigate normal gastric emptying time and gastrointestinal transit in Labrador dogs by means of a barium meal, observed by x-ray fluoroscopy. The results show that following a barium meal, the stomach of an adult Labrador remains at a high fill density up to 1 hour after ingestion and the small intestine remains at a high fill density between 2 and 5 hours.

Interpretive analysis of the fluoroscope images suggest that the stomach remains at a high fill density up to +1 hour after ingestion of a meal; that the first appearance of digesta in the stomach occurs at +30 mins; that the small intestine remains at a high fill density between +2 and +5 hours; and that the colon is at high fill density from +4 hours onward.

EXAMPLE 4

Figure 1A:
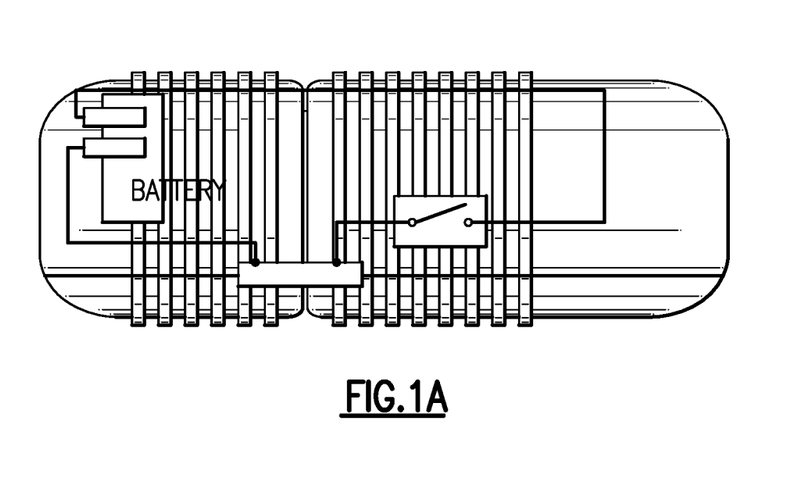
FIG. 1A is a schematic illustration of the device of the invention in closed compressed state.
Figure 1B:
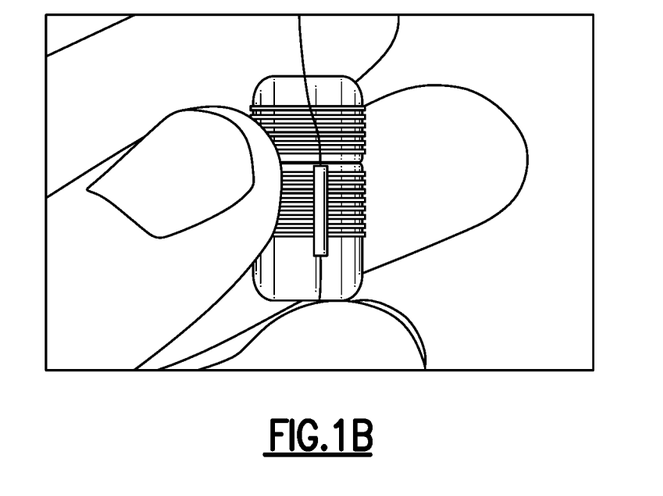
FIG. 1B is a photograph of the device in a closed compressed state.
Figure 2A:
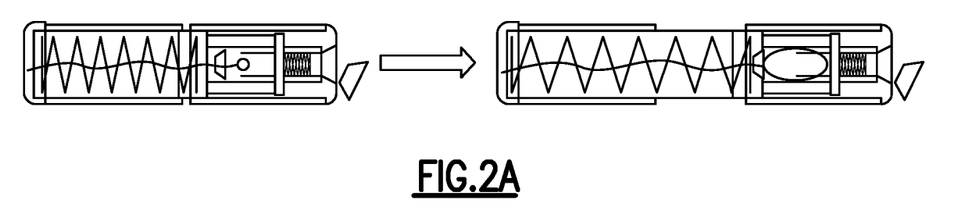
FIG. 2A is a schematic illustration of the device elongating from the closed compressed state to the open expanded state.
Figure 2B:
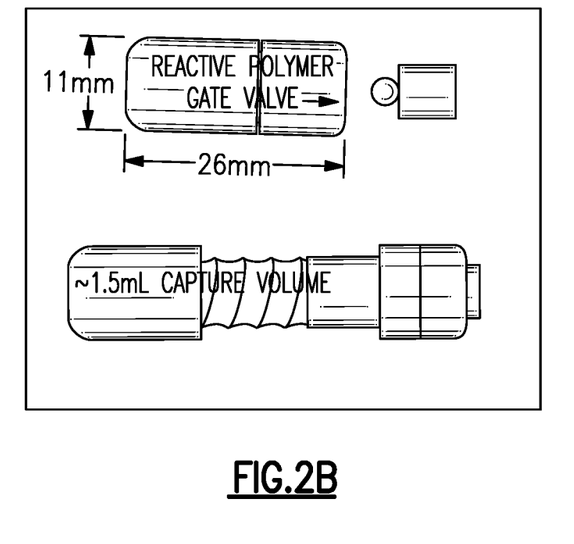
FIG. 2B is a schematic illustration of the device in an open expanded state.
Figure 3A:
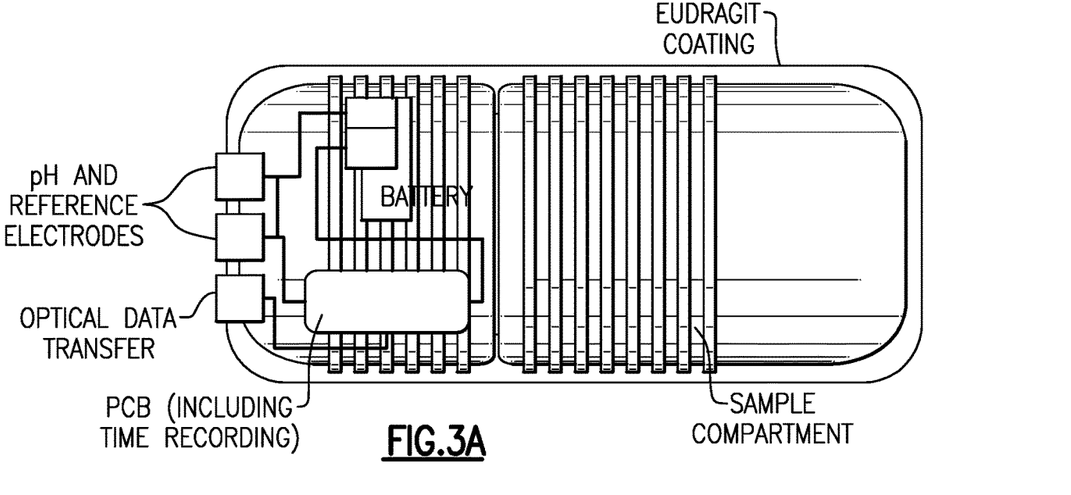
FIG. 3A is a schematic illustration of one of the embodiments of the invention, wherein the device comprises a pH sensor.
Figure 3B:
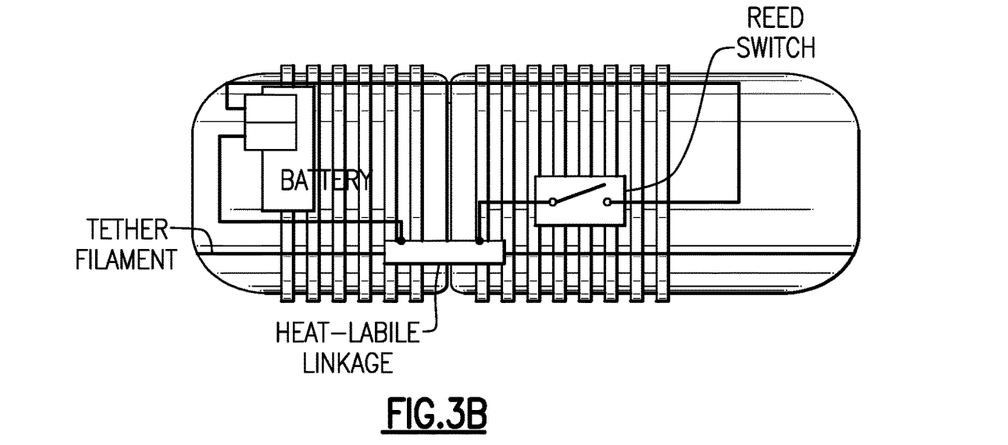
FIG. 3B is a schematic illustration of one of the embodiments of the invention, wherein the device comprises a tether filament and switch.
Figure 4:
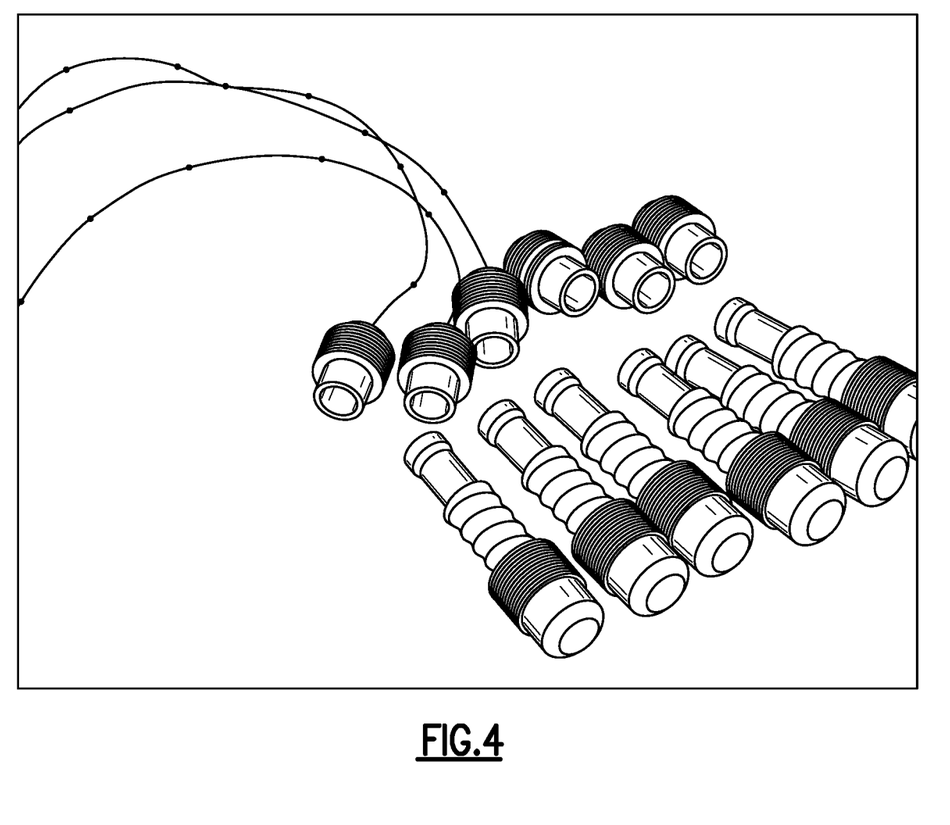
FIG. 4 is a schematic illustration of the device of the present invention.
Figure 5:
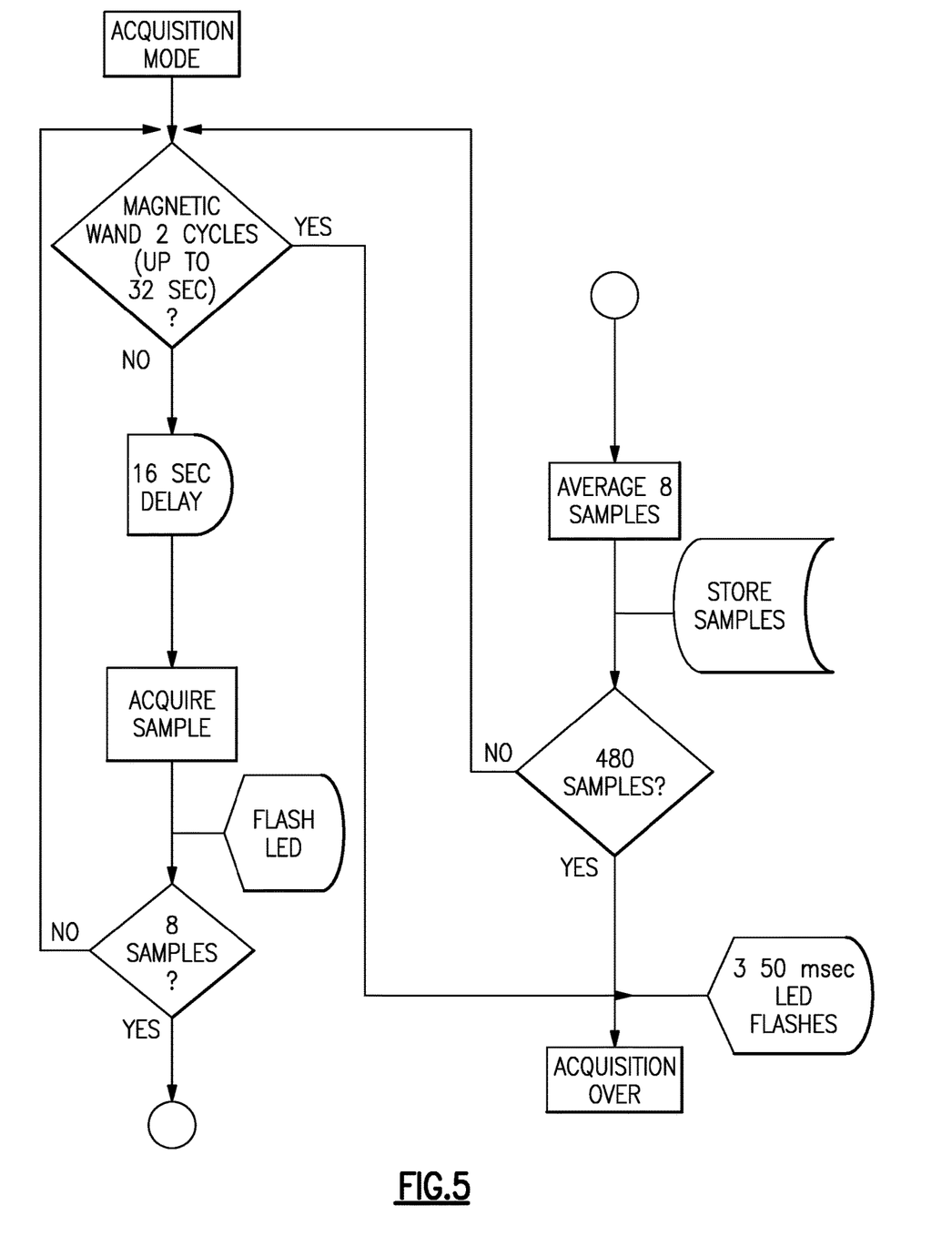
FIG. 5 is a schematic flow chart diagram detailing the process of activating the device of the present invention.

Details of the process for activating the device (see FIG. 5).

The capsules have sufficient battery power to remain in sleep mode for 100 days. From "Sleep mode" the capsules are activated by the presence of a magnet. Swiping a magnet across the capsule surface in SLEEP MODE will give a brief signal from the LED to determine whether the capsule is still functioning normally (e.g. no broken wires). 2 flashes=OK; 4 flashes=circuit failure.

After a 32 second delay, a second flash of 10 milliseconds indicates that the capsule is now in "Acquisition mode"

The capsule takes a reading from the pH electrodes every 16 seconds. Each reading is accompanied by a flash of the LED. After 8 readings have been taken (128 seconds) the pill calculates a mean value for the eight readings and stores this value in internal memory. The memory can store 480 of these mean values, giving 17 hours of data recording. After this time, the capsule goes into "pre serial sleep mode".

The capsule will collect data for 17 hours unless interrupted by the presence of a magnet. Holding a magnet against the surface of the capsule for 32s will put the capsule into "pre serial sleep mode". This is used in cases where the capsule is recovered prior to 17 hours having elapsed.

In the "pre serial sleep mode", the capsule waits for a magnet swipe before transmitting data. After a magnet swipe, the pill waits 16 seconds, then downloads the data through the LED at 300 baud. The LED is held against a light sensitive data recorder attached to a PC during data transmission.

The capsules are returned to "sleep mode" (reset) by holding a magnet against the surface of the capsule for a prolonged period (around 48 seconds). The capsule will flash 3 times after 32 seconds, after a further 16 seconds the capsule will give an extended single flash of four seconds, followed by 4 rapid flashes. The capsule is then back in "sleep mode".

The invention claimed is:

1. A reusable device for sampling internal substances in the gastrointestinal tract of an animal, said device comprising at least a first expandable sample collection chamber, the sample collection chamber having an aperture forming an external opening and an aperture closure comprising a polyacrylamide bead immobilized on a mesh screen operatively disposed relative to the aperture; a closure tab consisting of a pH sensor or a switch; a battery and associated electronic circuits in communication with the closure tab so that the operation of the closure tab may be externally controlled; and a resilient member; said device being held in a closed compressed state by the closure tab, wherein the first expandable sample collection chamber has a first volume when the device is in a closed, compressed state, and when the closure tab is actuated, the sample collection chamber is expanded by the resilient member to a second volume.

2. The reusable device of claim 1, consisting of the first expandable sample collection chamber, closure tab, battery and associated electronic circuits in communication with the closure tab, and resilient member.

3. The device of claim 1, wherein the resilient member comprises a spring.

4. The device of claim 1, wherein the expanded sample collection chamber can hold a volume of up to 5 ml.

5. The device of claim 1, wherein the length or diameter of the aperture is from 2 to 5 mm.

6. The device of claim 1, wherein the length of the device is from 5 mm×15 mm to 15 mm×30 mm in the closed, compressed state and/or from 5 mm×30 mm to 15 mm×50 mm in an open, expanded state.

7. A method of obtaining an internal substance and/or collecting data from the gastrointestinal tract of an animal, comprising orally administering a reusable device for sampling internal substances in the gastrointestinal tract to the animal, said device comprising at least a first expandable sample collection chamber, the sample collection chamber having an aperture forming an external opening and an aperture closure comprising a polyacrylamide bead immobilized on a mesh screen operatively disposed relative to the aperture; a closure tab consisting of a pH sensor or a switch; a battery and associated electronic circuits in communication with the closure tab so that the operation of the closure tab may be externally controlled; and a resilient member; said device being held in a closed compressed state by the closure tab, wherein the first expandable sample collection chamber has a first volume when the device is in a closed, compressed state, and when the closure tab is actuated, the sample collection chamber is expanded by the resilient member to a second volume; and recovering the device from the stool of the animal.

8. The method of claim 7, wherein the device is administered to the animal in a fasting state, with food, or at an interval after feeding.

9. The method of claim 7, wherein the animal is a human or a pet such as a dog, cat or horse or a farm animal such as a cow, sheep or a chicken.

10. The method of claim 7, wherein the device comprises a second expandable sample collection chamber, and wherein the first expandable sample collection chamber collects a first sample at a first determined point in the gastrointestinal tract and the second expandable sample collection chamber collects a second sample at a second determined point in the gastrointestinal tract.

11. The method of claim 7, wherein the device collects data from the gastro intestinal tract of the animal for up to 17 hours.

12. The method of claim 11, wherein the data comprises multiple readings from the pH sensor.

13. The method of claim 12, wherein the device calculates a mean of a number of the readings, and stores the mean in an internal memory.

\* \* \* \* \*